(12) United States Patent
Parmentier

(10) Patent No.: US 10,137,431 B2
(45) Date of Patent: Nov. 27, 2018

(54) MULTICAPILLARY MONOLITH

(71) Applicant: Francois Parmentier, Saint Martin d'Heres (FR)

(72) Inventor: Francois Parmentier, Saint Martin d'Heres (FR)

( * ) Notice: Subject to any disclaimer, the term of this patent is extended or adjusted under 35 U.S.C. 154(b) by 21 days.

(21) Appl. No.: 15/063,196

(22) Filed: Mar. 7, 2016

(65) Prior Publication Data

US 2016/0184800 A1    Jun. 30, 2016

Related U.S. Application Data

(62) Division of application No. 13/634,869, filed as application No. PCT/FR2011/000137 on Mar. 15, 2011, now Pat. No. 9,314,769.

(30) Foreign Application Priority Data

Mar. 15, 2010 (FR) ...................................... 10 01022

(51) Int. Cl.
*B01J 20/283* (2006.01)
*B01J 20/28* (2006.01)
(Continued)

(52) U.S. Cl.
CPC ........... *B01J 20/283* (2013.01); *B01J 20/284* (2013.01); *B01J 20/28045* (2013.01);
(Continued)

(58) Field of Classification Search
CPC .............................. B01J 20/283; B01J 20/284
See application file for complete search history.

(56) References Cited

U.S. PATENT DOCUMENTS 4,657,742 A    4/1987   Beaver
4,818,264 A    4/1989   Langhorst
(Continued)

FOREIGN PATENT DOCUMENTS

DE    102 29 339 A1    1/2004
EP        301948          1/1989
(Continued)

OTHER PUBLICATIONS

PTO Translation No. 13-5246 of Dubots (E.P. No. 301,948) dated Feb. 1989.
(Continued)

*Primary Examiner* — Timothy Kennedy
(74) *Attorney, Agent, or Firm* — Womble Bond Dickinson (US) LLP

(57) ABSTRACT

The invention relates to a monolithic porous material made of amorphous silica or activated alumina, comprising substantially rectilinear capillary channels that are parallel to one another, wherein:
 the channels have a substantially uniform cross-section relative to each other,
 the cross-section of each channel is regular over its entire length,
 the channels pass through the material from end to end,
 the length of the channels is equal to or more than 10 mm.
The invention also relates to an annular, radial or axial chromatographic apparatus, the packing of which consists of at least one said monolithic material.
The invention also relates to processes for manufacturing such a monolithic material.

9 Claims, 5 Drawing Sheets

(51) Int. Cl.
*B01J 20/284* (2006.01)
*B01J 20/30* (2006.01)
*G01N 30/60* (2006.01)
*B01J 20/281* (2006.01)
*G01N 30/52* (2006.01)
*G01N 30/00* (2006.01)

(52) U.S. Cl.
CPC ....... *B01J 20/28095* (2013.01); *B01J 20/305* (2013.01); *B01J 20/3078* (2013.01); *G01N 30/482* (2013.01); *G01N 30/6043* (2013.01); *B01J 2220/82* (2013.01); *G01N 2030/484* (2013.01); *G01N 2030/528* (2013.01)

(56) References Cited

U.S. PATENT DOCUMENTS

| | | | |
|---|---|---|---|
| 4,957,620 | A | 9/1990 | Cussler |
| 5,234,594 | A | 8/1993 | Tonucci et al. |
| 5,565,394 | A | 10/1996 | Lachman et al. |
| 5,864,743 | A * | 1/1999 | Tuchinskiy ........ B01D 39/2075 156/89.11 |
| 6,174,352 | B1 | 1/2001 | Semerdjian et al. |
| 6,210,570 | B1 | 4/2001 | Holloway |
| 6,333,088 | B1 | 12/2001 | Le Febre et al. .......... 428/36.91 |
| 6,562,744 | B1 | 5/2003 | Nakanishi et al. ............. 501/39 |
| 7,250,214 | B2 | 7/2007 | Walter et al. ................. 428/405 |
| 2001/0053530 | A1 | 12/2001 | Klein et al. |
| 2005/0023204 | A1 | 2/2005 | Nakanishi et al. |
| 2005/0139536 | A1 | 6/2005 | Belov et al. |
| 2006/0032816 | A1 | 2/2006 | Marcus et al. |
| 2006/0090649 | A1 | 5/2006 | Liu et al. |
| 2006/0090651 | A1 | 5/2006 | Liu et al. |
| 2007/0000508 | A1 | 1/2007 | Xue et al. |
| 2007/0134748 | A1 | 6/2007 | Kudo et al. |
| 2007/0207484 | A1 | 9/2007 | Brook et al. ...................... 435/6 |
| 2009/0107330 | A1 | 4/2009 | Gu .................................. 95/55 |
| 2010/0038298 | A1 | 2/2010 | Angelini et al. ........... 210/198.2 |

FOREIGN PATENT DOCUMENTS

| | | |
|---|---|---|
| EP | 0 301 948 A1 | 2/1989 |
| FR | 2 957 276 A1 | 9/2011 |
| WO | WO 95/28279 | 10/1995 |
| WO | WO 01/47634 A1 | 7/2001 |
| WO | WO 2008/143821 A1 | 11/2008 |

OTHER PUBLICATIONS

Nakanishi, K. et al., "Phase Separation in Gelling Silica-Organic Polymer Solution: Systems containing Poly(sodium styrenesulfonatc)", *J Am. Ceram. Soc.*, 74 (10) 2518-2530 (1991).

Ishikuza, N. et al "Designing monolithic double-pore silica for high-speed liquid chromatography", *Journal of Chromatography A*, 797 (1998) 133-137.

Mukai, S.R. et al, "Formation of monolithic silica gel microhoneycombs (SMHs) using pseudosteady state growth of microstructural ice crystals," *Chemical Communications*, XP-002607460, Mar. 4, 2004, pp. 874-875.

Nakanishi, K. et al., "Phase Separation in Gelling Silica-Organic Polymer Solution: Systems containing Poly(sodium styrenesulfonate)", *J. Am. Ceram. Soc.*, 74 (10) 2518-30 (1991).

Nakanishi, K. et al., "Phase Separation in silica sol-gel system containing polyacrylic acid—I. Gel formation behaviour and effect of solvent composition", *Journal of Non-Crystaline Solidd*, 139 (1992)1-13.

Nakanishi, K. et al., "Phase Separation in silica sol-gel system containing polyacrylic acid—II. Effects of molecular weight and temperature", l*Journal of Non-Crystalline Solids* 139, (1992) 14-24.

Nishihara, H. et al., "Ordered macroporous silica by ice templating," *Chemistry of Materials*, Feb. 28, 2005, pp. 683-689.

Nishihara, H et al. Synthesis of silica-based porous monoliths with straight monochannels using an ice-rod nanoarry as a template, *Journal of Materials Chemistry, The Royal of Chemistry*, GB, Aug. 21, 2008 XP 002604922.

Office Action in U.S. Appl. No. 14/344,600 dated May 23, 2017.

On et al. "Stability of mesoporous aluminosilicate MCM-41 under vapor treatment, acidic and basic conditions." Micropous and Mesoporous Materials, 1988, 22, pp. 211-224.

International Search Report in PCT/FR2012/000367 dated Dec. 21, 2012, with English translation English translation.

Janicke et al. "Low Silica MCM-41 Composites and Mesoporous Solids." Chem. Mater. 1999, 11, pp. 1342-1351.

Rosset et al. "Chromatographies en phases liquide et supercritique (Liquid and supercritical phase chromatographies)." Editions Masson, 1991, pp. 224-226, with brief explanation in English of relevance of reference.

U.S. Office Action dated Jun. 11, 2015, U.S. Appl. No. 14/344,600.

U.S. Office Action dated Oct. 12, 2016, U.S. Appl. No. 14/344,600.

Babin et al., "MCM-41 silica monoliths with independent control of meso- and macroprosity." New J. Chem., 2007, 31, 1907-1917.

* cited by examiner

MULTICAPILLARY MONOLITH

FIELD OF THE INVENTION

The present invention concerns a monolithic porous material of amorphous silica or activated alumina, comprising substantially rectilinear capillary channels that are parallel to one another, passing through the material from end to end and intended in particular for use in chromatography.

BACKGROUND OF THE INVENTION

The close contact between two phases such as a gas and a liquid to promote their chemical or physical interaction is an important operation in chemical engineering.

To promote interface phenomena on the contact surface between these two phases, it is endeavoured to increase this contact surface as much as possible, and to increase the effects of mixing in the vicinity thereof.

For such purpose, beds of fine solid particles are frequently used through which a fluid passes and with which they interact.

These beds, called particle beds or packings, offer large exchange surfaces on account of the small size of their constituent particles, and on account of the large divided status of the fluid passing through them.

These phenomena promote the speedy accomplishing of material transfer processes, chemical reactions or any other diffusion-related phenomena.

Their applications particularly cover the fields of both analytical and preparative liquid and gas chromatography.

U.S. Pat. No. 4,657,742 to Beaver P. proposes an alternative to these particle packings comprising a tube packed with aligned fibres which may be porous and hollow. One disadvantage of this packing is that the eluting fluid flows both inside and outside the hollow fibres in the voids left between their stacking. Since the eluting fluid flows at two very different rates inside the hollow fibres and on periphery thereof in the interstices separating the fibres of circular section, there is resulting loss of efficacy. Another disadvantage of this device is that the walls of the hollow fibres must be sufficiently thick so that they can be handled and packed withstanding the mechanical stresses induced by the stacking thereof. This means that the diffusional balancing between adjacent fibres is slow, and the packing is little efficient. Another disadvantage of this device is that it is difficult to apply to bundles of fibres of large diameter since the chemical stability of the packing would be difficult to ensure.

Patent U.S. Pat. No. 4,957,620 to Cussler E. describes the use of bundles of hollow polymer fibres for use as chromatographic column. The assembly suffers from the same disadvantages as above: the thickness of the wall of the fibres must be higher than that of the central channel in order to impart sufficient mechanical strength to these fibres allowing the handling and assembly thereof. As a result, transfers of material by diffusion between the material of the walls and eluting fluent are slow. The eluting fluid flows at two very different rates inside the hollow fibres and on the periphery thereof. Here again the stabilization of large diameter packing is difficult owing to the lack of strong bonds between adjacent fibbers.

Patent U.S. Pat. No. 4,818,264 describes the use of bundles of capillary columns in glass or silica to perform multicapillary gas chromatography. This system has the serious drawback that the capillaries behave independently of each other. On this account, it is difficult to obtain identical behaviour of the different channels and careful, scrupulous attention must be given to the manufacture of channels that are all identical.

Patent application US 2005/0139536 to Belov Y. P. describes a chromatographic column whose channels are coated with different thicknesses of stationary phase so as to offset hydrodynamic inequalities between the different channels. This work exemplifies the difficulty in obtaining good performance levels with a multicapillary column formed of individualized channels which do not communicate by diffusion.

The publications by Nishihara H. «Ordered macroporous silica by ice templating», Chemistry of Materials, 28 Feb. 2005, pages 683-689 and Mukai S. R. «Formation of monolithic silica gel microhoneycomb (SMH's) using pseudo steady state growth of microstructural ice crystals» Chemical Communications, 4 Mar. 2004, pages 874-875 describe a potential pathway for forming multicapillary structures in silica. The documents refer to a method of manufacturing microstructures of ordered porous silica, of honeycomb shape and 3.6 to 40 µm in diameter. The method comprises causing directional growth of ice crystals in low-cohesion silica gels and evaporating a solvent by freeze-drying.

However, the described method only functions with silica gels having low cohesion i.e. with low silica concentration. The structures obtained are therefore very lightweight, namely having a density of the order of 0.12 g/cm$^3$ according to the authors of these publications. The relative volume of the capillaries is high. As such, they will not perform well in liquid chromatography for which a dense packing is sought having strong retention capacity. In addition, packing that is so lightweight is mechanically fragile.

Additionally, examination of all the photographs in the two articles shows that the diameters of the channels differ by a factor of about 10, and that these channel diameters fluctuate to a large extent and are irregular over their length. These channels have most variable environment and morphology, their cross-section possibly being square, pentagonal, hexagonal, etc. These irregularities mean that such packing is inefficient for high performance analytical chromatography for which perfect homogeneity of the packing is required.

Finally, the packings described in these articles are obtained over a restricted range of diameters, from 3.6 to 42 µm. Yet, the range extending below 2 µm is of particular interest for application in high pressure liquid chromatography (HPLC), and the range extending above 50 µm is of particular interest for application to gas chromatography.

Patent U.S. Pat. No. 6,210,570 to Holloway R. describes monolithic packing in porous silica for chromatography. Said packing is formed of more or less spherical pores forming tortuous passages through the packing. These passages are tortuous and a fluid passing them encounters numerous obstacles, the pores and the solid being randomly distributed in space within the packing. This forms a major difference with a flow through an empty capillary tube in which the fluid does not encounter any microscopic obstacle over an optimal rectilinear pathway. They display a lower pressure drop than a particle packing but higher than that of a capillary having the same separation efficacy for a given analysis, and have intermediate separation impedance between the two. They have the advantage of allowing a macroscopically uniform flow of the eluting fluid through the packing on account of their monolithic structure, unlike the case with the stack of capillary tubes described in U.S. Pat. No. 4,657,742.

The following publications: N, Ishizuka, Designing monolithic double pore silica for high speed liquid chromatography, Journal of Chromatography A, 797 (1998), 133-137, K Nakanishi, Phase separation in silica sol-gel system containing polyacrylic acid, Journal of non crystalline Solids 139 (1992, 1-13 and 14-24, K. Nakanishi, Phase separation in Gelling Silica-Organic Polymer Solution: Systems Containing Poly(sodium styrenesulfonate), J. Am. Ceram. Soc. 74 (10) 2518-2530-30 (1991) deal with the same subject matter as the Holloway patent. The aim is to obtain a monolithic packing in silica comprising two families of pores, one of interconnected macropores in which a liquid is able to flow relatively freely and the other a family of mesopores or micropores creating a specific surface area and hence activity for the exchange of material.

However, the large majority of separations are still conducted on particle beds, which are easier to manufacture.

There is therefore a need for a product having advantages in terms of reliability and ease of manufacture of particle packing, allowing the uniform microscopic and macroscopic flow of eluting fluid in the bed, whilst maintaining the advantages of capillary columns.

BRIEF DESCRIPTION OF THE INVENTION

For this purpose, the invention proposes a monolithic porous material based on amorphous silica or activated alumina, comprising substantially rectilinear capillary channels parallel to one another, characterized in that:
the channels have a substantially uniform cross-section in relation to one another,
the cross-section of each channel is regular over the entire length thereof,
the channels pass through the material from end to end.

Advantageously, the length of the channels is equal to or greater than 10 mm, preferably greater than 20 mm and further preferably greater than 50 mm.

By «based on» is meant that the structure of the monolith is essentially formed of amorphous silica or activated alumina, optionally surface-modified.

By «substantially uniform cross-section» is meant herein that the diameters of the different channels are close to each other i.e. in particular that the mean diameter of one channel does not on average differ by more than 30% from the average of the diameters of the channels.

The standard deviation of the diameter of the channels is less than 30% from the mean, preferably less than 5%.

By «regular cross-section» is meant that the channels respectively have a substantially constant cross-section over their entire length, i.e. the diameter of a channel does not vary by a factor of more than 2 between the narrowest regions and the widest regions.

The material advantageously has a density of more than 0.12 kg/liter.

In particularly advantageous manner, the material has a relative volume of the capillary channels that is less than 90%.

The thickness of the wall between two adjacent channels, in its narrowest part, is advantageously less than one half of their diameter.

According to one embodiment of the invention, the capillary channels have a diameter of between 0.1 and 1.5 micrometers.

According to another embodiment of the invention, the capillary channels have a characteristic diameter or cross dimension of more than 50 µm.

The material is advantageously formed of amorphous silica, which may or may not be silane-modified on the surface, or of an alumina $\gamma$, $\chi$, $\kappa$, $\eta$ or $\theta$ which may or may not be surface modified.

The monolithic material advantageously has an elongate shape characterized by a length (i.e. the length of the capillary channels) greater than its dimension in a direction perpendicular to the channels.

A further subject of the invention is a chromatographic column whose packing comprises at least one monolithic porous material such as described above.

Advantageously, the monolith is sufficiently long so that a single monolith is sufficient for application in chromatography.

Optionally, several monoliths can be stacked.

A further subject of the invention is an axial, continuous annular chromatographic instrument in which the packing comprises at least one monolithic porous material such as described above.

A further subject of the invention is a radial, continuous annular chromatographic instrument in which the packing comprises at least one monolithic porous material such as described above.

The invention also concerns a process for manufacturing a monolithic porous material in amorphous silica or activated alumina comprising substantially rectilinear capillary channels parallel to one another, characterized in that it comprises the steps of:
providing a bundle of so-called precursor fibres of the channels whose diameter is equal to the diameter of the capillary channels,
forming a porous matrix of amorphous silica or activated alumina around the fibres,
eliminating the fibres so as to form said capillary channels in said matrix.

Optionally, the precursor fibres of the channels comprise an ablative layer of coating material which is eliminated at a first treatment step for fibre removal.

According to one particular embodiment of the invention, the precursor fibres of the channels optionally comprising their coating of ablative material are coated with a spacer before forming the bundle so as to ensure a minimum thickness of monolith between two adjacent channels.

According to one embodiment of this method, the fibres are formed of a hydrolysable polymer, the fibres are assembled in a bundle, the bundle is immersed in a silica gel precursor solution, this solution being caused to gel around the fibres, and the fibres are removed by hydrolysis to soluble species of low molecular weight.

By «silica gel precursor solution» is meant a liquid whose composition is such that as it develops under the conditions of the manufacturing process, it leads to a silica gel.

According to another embodiment of this method, the channel precursor fibres are of wire fibre with low melting point coated with a film of silica or activated alumina, assembled into a bundle, the bundle is immersed in a silica gel or activated alumina precursor solution, this solution being caused to gel around the fibres and the fibres are eliminated by melting and draining the molten liquid outside the material.

If the material is amorphous silica, this amorphous silica can be reinforced by depositing silica on the surface of its constituent particles before it is dried.

According to one embodiment of this process, the porous matrix of amorphous silica has a high proportion (i.e. preferably higher than 40%) of macropores allowing the circulation of a fluid within the monolith.

Alternatively, the invention proposes a process for fabricating a monolithic porous material of amorphous silica comprising substantially rectilinear capillary channels that are parallel to one another, comprising the steps of:
- forming channels in at least one sheet of a silicone elastomer,
- stacking or rolling this or these sheets so as to form conduits which will form capillary channels,
- pyrolysis and oxidation of the silicone to amorphous silica.

BRIEF DESCRIPTION OF THE DRAWINGS

Other characteristics and advantages of the invention will become apparent from the following detailed description with reference to the appended drawings in which.

DETAILED DESCRIPTION OF THE INVENTION

Figure 1:
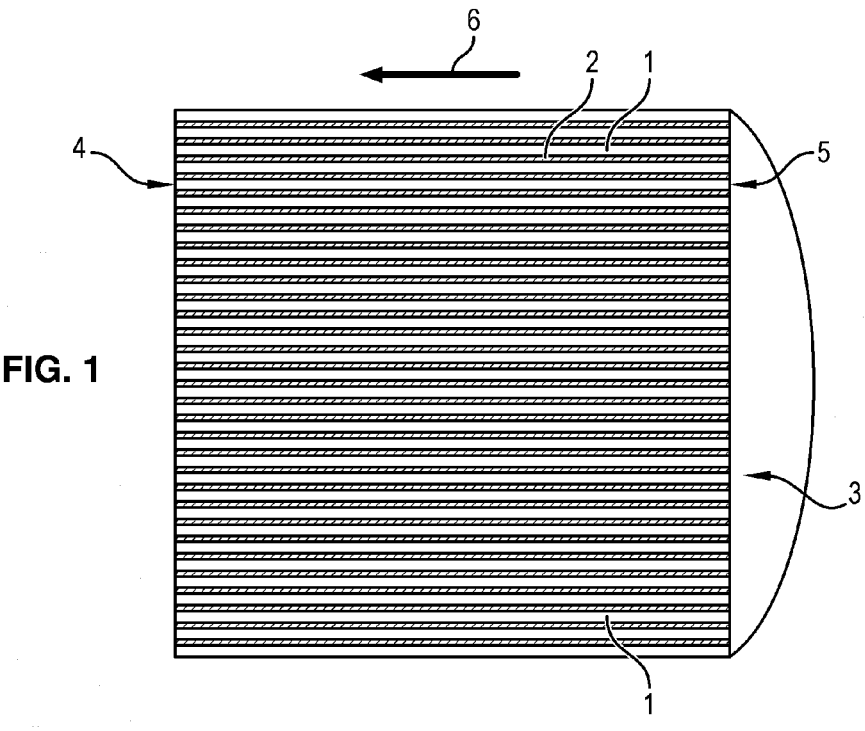
FIG. 1 is a cross-sectional view of a cylindrical multi-capillary packing for chromatography according to the invention, following a direction perpendicular to its major axis.

The invention allows a structure to be obtained that is capable of competing with particle packing, in the diversity of applications thereof and in particular in chromatography.

The monolithic material is a solid (amorphous silica or activated alumina) that is essentially porous and comprising a multiplicity of rectilinear, contiguous channels that are parallel to one another, which are channels of capillary dimensions i.e. a diameter not exceeding a few millimeters) and which impose a preferable direction for the fluid in the bed. The porous mass offers a large exchange surface between the fluid and the solid, which may be an adsorbent or the medium of a stationary phase.

The porous nature of the solid allows exchange of material by diffusion between the adjacent channels, therefore allowing concentration gradients to be reduced between neighbouring capillary channels and a reduction in their irregularities.

These irregularities are due to small differences in terms of topology and diameter between the different channels.

The monolithic structure of the packing obtained also allows the ensured transiting of the entirety of the fluid through the core of the channels without any other possible pathway, and the ensured mechanical cohesion of the packing.

A monolith can be defined as follows: a structure having a multiplicity of channels of capillary dimensions operating in parallel crossing through a mechanically cohesive mass of porous material from end to end.

The monolith may be of any suitable length for the process to be carried out, between a few millimeters and several meters.

The monolith may have a cross-section that is suitable for the process to be carried out, between a few square micrometers and several square meters.

Two main mineral oxides are known for achieving chromatographic separations: amorphous silica and activated alumina. The first is a silicon oxide, and the second is an aluminium oxide. These two oxides have numerous points in common, in particular:
- they can be obtained in the form of solids with high specific surface area, several hundred $m^2$ per gram;
- they can be shaped using the sol-gel route;
- they have a very active surface for the adsorption of organic molecules, making them selective for a chromatographic separation process.

The packing materials of the invention are therefore preferably composed of amorphous silica or activated alumina.

According to the invention, the cross-sections of these channels are regular and uniform i.e. the channels respectively have a substantially constant cross-section over their entire length and diameters of close size.

By regular or substantially constant cross-section is particularly meant a diameter which does not vary by a factor of more than 2 between the narrowest regions and the widest regions of one same channel.

By diameters of close size is particularly meant that the mean diameter of a channel does not on average differ by more than 30% from the average of the diameters of the channels.

In other words, and if it is assumed that the diameters of the channels are distributed according to a reduced centred normal law, the standard deviation must preferably not exceed 30%. Preferably, this standard deviation does not exceed 5% and further preferably 0.5%.

Preferably the channels have a constant and uniform arrangement and shape.

According to one preferred embodiment of the capillary channels, the channels preferably have a substantially circular cross-section.

However, the channels may assume different geometric shapes, in accordance with the method of manufacture of the fibres used for fabrication thereof. These geometric shapes may be a circle, a square, a polygon with substantially equal sides. The diameter of the channel in this case is the diameter of the circle inscribed within this geometric shape.

According to one preferred embodiment of the invention, the multicapillary packing contains a high proportion of solid.

A high volume proportion of a solid with a high specific surface area increases packing capacity and requires a smaller volume of bed.

In particular, this proportion is such that its density is greater than 0.12 kg/liter and is preferably greater than 0.15 kg/liter.

In even further relevant manner, these packing materials are defined by the proportion of volume occupied by the capillary channels in the monolith. In this text, this ratio will be called the «relative volume of the capillaries».

Preferably the relative volume of the capillaries is less than 90%, more preferably less than 80% for analytical applications. For preparative chromatography applications, the relative volume of the capillaries may be much lower, preferably but not limited thereto less than 40%, more preferably less than 20%, so as to increase the packing capacity to a maximum.

Preferably, the wall separating the adjacent parallel channels at its narrowest point has a thickness less than one half of their diameter or of their characteristic transverse dimension.

Preferably, the walls separating the channels are regular in dimension and in arrangement.

Preferably, for absorption processes, the gel forming the monolith comprises a high volume of mesopores of diameter 4 nm to 25 nm, so as to create a specific surface accessible by diffusion.

The porous volume measured, excluding the volume of the channels, may for example be between 0.3 and 3 cm$^3$/g for silica and between 0.2 and 0.5 cm$^3$/g for alumina.

For silica, if bimodal gels are used such as those described in the Holloway patent and in the publication by N, Ishizuka, the porous volume may be notably higher when including the macropores.

Preferably, for absorption processes the gel forming the monolith has a high specific surface area, of between 90 m$^2$/g and 600 m$^2$/g for example, for silica and alumina.

Preferably, for implementation of the invention, the monolith has a high number of channels, for example more than five, preferably more than fifty, further preferably more than five hundred.

It is noted that the pressure drop in a multicapillary packing is of one or two orders of magnitude smaller than in a bed of particles of same characteristic dimension. This results from expression of the laws of Darcy and Poiseuille.

Therefore, the separation impedance of a multicapillary packing in chromatographic separation may be increased by one or two orders of magnitude compared with a particle packing.

The multicapillary packing comprises a large number of capillaries of equal length and mean radius R. It is considered that the diameter statistically follows a normal law with a standard deviation $\sigma_R$. It can be calculated that for this multicapillary packing the maximum number of theoretical plates of chromatographic separation which can be obtained is written:

$$N_{R,max} = R^2/(9 \cdot \sigma_R^2)$$

For example, if the relative standard deviation is 1%, the maximum number of plates of the separation will be $1.1 \cdot 10^5$. If this diameter has a relative standard deviation of 1%, 1100 plates are already available which is sufficient for numerous chromatographic separations.

The results can in fact be improved if the channels are not perfectly individualized but are closely stacked or close to each other with sufficiently thin walls separating them such that the transfer of material takes place between each channel and its closest neighbours.

This can be achieved by fabricating the multicapillary packing in a partly or fully porous mass allowing each channel to equilibrate with its neighbours via diffusion. The resulting effect, whose calculation depends on the spatial arrangement of the capillaries, will be an attenuation or damping of the difference in behaviour of the individual channels, owing to transfers of diffusive material from one channel to another.

The observed resulting effect is an increase in efficacy, the random variations in the diameters of the channels being averaged out by the diffusion process.

According to another advantage of the invention, the porous mass is the medium of a stationary phase for chromatography or itself forms the stationary phase through its high specific surface area.

According to another advantage of the invention, the much smaller pressure drop through a multicapillary packing of equal characteristic dimension allows a strong increase in separating power.

The pressure drop of a particle bed follows Darcy's law. The pressure drop of a multicapillary packing follows Poiseuille's law.

The pressure drop of a liquid phase (water at ambient temperature) for a bed of particles of diameter 5 μm is 250 bar/m, and for capillaries of diameter 5 μm it is 18 bar/m at an eluting rate of 1 mm/s relative to the total cross-section of the column. The void fraction of the multicapillary packing is assumed to be 0.7.

The pressure drop of a multicapillary packing of length 100 mm in this case is only 1.8 bar.

This in fact means that much narrower capillaries can be used and that the speed of analysis and efficacy can simultaneously be considerably increased in existing analytical chromatic equipment.

These different packing materials show linear dependence of pressure drop on eluent velocity and length.

The separation impedance E is given by the formula:

$$E = t_0 \cdot \Delta P/(N^2 \cdot \eta)$$

For a particle packing, it is 2350.
For a multicapillary packing, it is 115.

A multicapillary packing is higher by two orders of magnitude in terms of impedance and separation. As mentioned previously, this means that very small capillaries can be used with high pressure pumps and their peripherals and analysis speeds and efficacies can be increased by one order of magnitude.

For example, a multicapillary packing for HPLC can be proposed as follows: in liquid phase for a given pressure drop, for a given number of required theoretical plates, the diameter $d_c$ at optimal efficacy will be written as follows for a single capillary:

$$d_c = (128 \cdot \eta \cdot N \cdot D/\Delta P)^{1/2}$$

For a pressure drop of between 80 and 180 bars, and high efficacy of 100 000 plates, the following equation can be drawn:

$$d_c = 0.84 - 1.46 \text{ μm}$$

From a practical viewpoint, a packing for liquid phase analytical chromatography may comprise a bundle of thousands of capillaries of diameter from 0.1 a 5 μm, and preferably a diameter of 0.1 to 1.5 μm separated by walls having a thickness of 0.05 to 1.0 μm thickness in porous silica or alumina of high specific surface area.

Also, for gas chromatography, the channels are preferably given a diameter of more than 50 μm so as to maintain an acceptable pressure drop.

The invention preferably concerns a packing for which the porous mass has a surface area of more than 20 m$^2$ per gram.

The diameters of the capillaries are preferably distributed following a normal law having a mean standard deviation of less than 0.5%.

The minimum elution time at optimal efficacy is 10 to 30 seconds for a column of length 100 mm, allowing very rapid and very efficient analyses compatible with the response times of existing detectors.

The packing allows a specific analysis speed of 3300 to 10000 plates per second.

So that the feed rate is from 0.8 to 2.6 μl/mn, compatible with the pumping system developed for packed microcolumns, 3000 to 10000 capillaries must be arranged in parallel. Higher feed rates can be ensured by simply increasing the number of capillaries in parallel and the cross-section of the packing.

For good efficacy of these structures, the homogeneity and regularity of the final packing must be as good as possible. The porosity of the walls of the channels must be high, the void fraction best being 30 or 40% or even higher. The thickness of the walls of the channels must be as narrow as mechanically possible to increase the speeds of diffusion phenomena.

Also, the very low pressure drop of a multicapillary packing allows the practical obtaining of devices which up until now have remained without any notable use.

A multicapillary packing can be seen as the assembly of a large number of adjacent chromatographic columns.

The chromatographic packing allows the obtaining of a tool that is both flexible and easy to use for performing preparative chromatography, continuous annular chromatography, in addition to conventional techniques of simulated mobile bed type.

A standard apparatus for continuous annular chromatography comprises:
   an annular cylinder of multicapillary packing whose channels lie parallel to its major axis. The two ends of this packing are planar and perpendicular to its axis and act as support for the fluid inlet and outlet assemblies.
   Fluid inlet and outlet assemblies comprise separated angular sectors which are fed with mixture to be separated or with eluting solvent on the inlet side, and collect the different eluted fractions on their outlet side. The walls delimiting the feed and collecting sections are either in contact with the packing via a seal sliding on the surface thereof, or they are positioned very close to the cylindrical packing (within a few micrometers for example) but not in contact therewith.

The inlet and outlet assemblies are fixed relative to one another for a given separation at a given time.

The packing cylinder and the group formed by the inlet and outlet assemblies move relative to one another in a movement of revolution about the axis of the packing cylinder.

This movement may be imposed upon the packing by a shaft to which it is attached. In this case the packing rotates in an outer ferrule machined so as to leave slight play between the packing, or a protection containing the same, and the ferrule under consideration.

Alternatively, it is the packing which is immobile and the inlet and outlet assemblies are set in rotation.

The charging of the mixture to be separated and of the eluting fluid is made through the different inlet sectors on the upstream side of the packing.

The collection of the separated fractions is similarly performed on sectors of the downstream surface of the packing.

The constancy of residence time of each component in the packing allows the collection thereof at defined, constant, angular distances of the inlet sector.

The continuous feeding of the inlet sector, under these conditions, produces continuous collection of the separated components in the outlet sectors.

The use of multicapillary packing materials in continuous annular chromatographs allows the lateral diffusion of the elution bands to be minimized to its pure diffusive component.

This is an important difference with devices formed of particle packing materials.

This leads to an increase in separating power measured in NUT or NETP compared with particle packing materials of the prior art.

Without departing from the scope of the invention, the capillary channels may be in the form of slits or bands.

In very similar fashion, it is possible to use the packaging materials of the invention in continuous radial chromatography.

In this case, the multicapillary packing is conformed as a cylinder in which the capillary channels extend radially and not axially. Their operating principle is very close to that just described (see also FIGS. 4, 5 and 6), the eluting fluid and the compounds to be separated in this case flowing inside the cylinder towards the outside of the cylinder, or vice versa. The feed and collecting sectors, in this case, are axial bands moving continuously relative to the annular cylindrical packing.

Continuous annular chromatography particularly allows the separation of a large number of components having very close retention times, such as isomers, optical isomers, position isomers, etc. . . . in a single pass in a single instrument, or in several passes in instruments placed in cascade with or without intermediate re-concentration of the eluates.

The multicapillary packing materials of the invention can be manufactured using any method known in the prior art and using the novel processes described below. The following processes are particularly well adapted.

One first process consists of covering and coating a bundle of fibres with a solid matrix material and of destroying or removing the material of the fibres so as only to leave the coating matrix subsisting through which the capillary channels pass.

The fibres are therefore the precursors of the capillary channels.

The fibres can be removed by mechanical action, by fusion, vaporisation, dissolution, chemical attack, etc. . . . .

Since the fibre acts as mould for the final capillary, very tight manufacturing tolerances thereof allow very regular capillaries to be obtained down to micron sizes using well known monofilament production techniques, and therefore excellent performance levels of separation can be reached. Submicron fibres exist. Nanometric fibres are in the course of being developed. Schematically the aim is to prepare a composite material of which only the matrix is left to subsist.

A process according to the invention therefore comprises the steps of joining the precursor fibres of the capillary channels with a binder, thereby creating a matrix around the precursors, and removing the core of the precursor fibres supporting the matrix by any means, oxidation, chemical attack, fusion and draining of the liquid, gasification so as to leave the matrix which can be used as base for chromatographic packing.

One simple solution consists of assembling a bundle of hydrophilic fibres of the required diameter, immersing same in an aqueous solution or suspension of a silica gel or alumina precursor solution whose polymerization and/or the gel are ensured in situ.

In the present text, by «silica gel precursor solution» is meant a liquid of composition such that its development under the conditions of the manufacturing process leads to a silica gel. In particular, it may be:
   an acidified aqueous solution of an alkaline silicate,
   an aqueous solution of an alkaline silicate whose metallic ions have been absorbed and exchanged with H+ ions by an ion exchange resin in its acid form, a silica sol prepared by precipitation-growth of monomer or weakly polymerized silica in a slightly basic aqueous phase on nuclei to form spherical nanoparticles, an aqueous solution at determined pH of an organometallic molecule derived from silicon such as an alkoxysilane e.g. tetraethoxyysilane, or tetramethoxyysilane.

Similarly, by «alumina gel precursor solution» is meant a liquid of composition such that its development under the conditions of the manufacturing process leads to an alumina gel.

The small contact angle between the material of the fibre and the solution promotes the creation of a film of homogeneous solution between the fibres.

To form the capillary channels, the fibres are hydrolyzed in an acid medium for example or carbonized and burnt.

Packing materials of porous silica and grafted porous silica can be obtained in this manner.

Packing materials of activated alumina can be obtained following the same scheme.

For improved quality and homogeneity of the packing obtained, it may be useful to start by coating the fibres with a jacket layer of a coating material called spacer material before assembling into a bundle.

It is possible that bare fibres may touch one another at contact points or lines and this will generate points of weakness and non-homogeneity in the packing.

In this case the process comprises coating a metal or non-metal fibre with a thickness of adequate coating material called a spacer, then joining these fibres into bundle optionally with a binder, and selectively eliminating the material of the fibres by fusion, dissolution, vaporisation, chemical attack, etc.

In particular, the spacer may be porous and is partly or fully integrated in the final monolith.

The jacket or layer of spacer coating material can be deposited by co-extrusion of a core fibre with a polymer or a gel.

It can be deposited by immersing in a solution of a polymer, or oligomers subsequently treated by thermal polymerization or UV and cross-linking.

The jacket may be formed of a chemical deposit (metal, oxide), deposited by vapour phase, plasma spraying, vacuum evaporation, liquid phase deposit. It can be deposited or sprayed using electric or electrostatic fields for non-conductive materials, the fibre being electrified to a certain potential, and a spacer powder being electrified to a potential of opposite sign and placed close to the fibre so that it can be deposited thereupon. It can be deposited by a printing technique of inkjet type. It may be formed of an agglomerated powder or gel deposited by passing through a bath or liquid suspension.

The spacer may be formed of a powder deposited in a thin film from a suspension, or of any material able to be deposited in a film.

In particular, it may be made by immersing the fibre in a suspension containing at least two constituents, first a powder mesoporous or microporous solid mineral, silica gel or activated alumina, and second a mineral binder, silica or alumina sol respectively.

The first constituent carries the chromatographic separating function and can be obtained by any known method, the function of the second constituent being to bind the solid particles mechanically together allowing handling of the coated film and its assembly into a bundle.

The binding action can be ensured by the sol gel, by drying, or by its gelling followed by drying thereof.

Preferably, and so as not to clog the possible mesopores and micropores of the powder mineral solid, as mineral binder a sol is used whose elementary particle size is greater than that of the mesopores.

It is possible in particular to ripen the sol under conditions causing its partial aggregation before mixing it with the mesoporous or microporous mineral solid.

For silica, this ripening can be conducted in a manner well known in the state of the art by combining pH, temperature and ionic strength of the sol medium.

Finally, it is possible to use relatively dilute binder sols.

One or more organic texturing additives, or binders can be added to the immersion suspension so as to impart sufficient mechanical strength to the fibre for handling and shaping thereof.

These additives may form part of the final monolith or they may be removed at a subsequent phase of the process.

The mechanical strength of the spacer can be ensured by sintering if the fibre withstands high temperatures (as is the case for iron or steel fibre for example).

The silica is used in its amorphous state.

For alumina, which exists in numerous crystallographic forms that are more or less active and more or less crystallized, preferably alumina gels are used prepared from trihydrates (hydrargilite ou bayerite) or monohydrates (boemite) activated by controlled calcining to a transition alumina, in particular the aluminas $\gamma$, $\chi$, $\kappa$, $\eta$ or $\theta$.

Preferably, the packing is made in a single allotropic variety of alumina, so that all the sites behave in the same manner with respect to the constituents of the mixture to be separated.

In particular, if the packing is composed of a powder deposited in an agglomerated suspension by a gel, it is desirable that the powder and gels should be activated to identical species after calcining.

Alternatively, in this same situation, it is possible to choose and to synthesize the reinforcing gel so that its specific surface area after activation is small and negligible compared with that of the powder alumina.

Following another process, to avoid contact of the channel precursor fibres, these are assembled into a sheet by weaving.

If the precursor fibre is the warp, the weft fibre is used as spacer, and conversely.

The fibre perpendicular to the precursor may be a glass fibre, which has good thermal compatibility in terms of expansion coefficient with the porous mineral material of the monolith.

The chemical inertia of a glass fibre is excellent and comparable with that of silica.

Since its specific surface is small it does not perturb analysis.

The fibres are assembled into a bundle and may be glued to each other.

The removal of the core of the fibres must be carried out so as not to destroy their matrix and/or their jacket layer. A choice can be made between several techniques, in particular:

By heating the assembly up to the melting temperature of the core material of the fibres, and removing the liquid under a pressure gradient. Easy melt metals such as tin, lead, bismuth, antimony, the alloys thereof (so-called Newton, Darcet alloys, etc.), or thermoplastic resins such as polyethylene, polypropylene, PVC, etc. allow the operation to be conducted at low temperature, from 70 to 200° C. for example. In this case, the jacket or matrix and the material of the fibres must be as compatible as possible in terms of thermal expansion, between the manufacturing temperature and the melt temperature. This method allows the core material to be recycled.

By forming fibres of a hydrolysable polymer, assembling the fibres into a bundle and immersing the bundle in a precursor solution of a mineral oxide, the solution being caused to gel around the fibres, and eliminating the fibres by hydrolysis to soluble species of low molecular weight. This manufacturing process is also characterized in that the gel can be reinforced by deposit via amorphous or crystalline growth of the mineral oxide on the surface of its constituent particles to increase its mechanical strength before drying.

If the spacer and the matrix are porous and allow the impregnation or circulation of a reagent through the assembled bundle, and contact thereof with the core material, its removal can be achieved by dissolution, chemical reaction, in liquid or vapour phase, etc. . . . . This operation can be conducted at moderate temperature, thereby avoiding problems of thermal expansion. For example, it is possible to use the formation of soluble or gaseous metallic chlorides, by direct action of the chlorine on iron fibres or by thermal degradation of polymers to their monomers as is the case with acrylic resins (PMMA), etc. . . . .

According to one variant of this method, the fibres are assembled parallel to each other in a plane or sheet and agglomerated with a porous or fibrous binder, or woven, so that they are conformed into a thin sheet. A flexible sheet is obtained by arranging the fibres of the binder perpendicular to the channel precursors. Chemical attack of the core of the channel precursor fibres can be performed via upper and lower sides of the sheet. This sheet can then be chemically treated etc. according to use and stacked or rolled in any arrangement.

The attack of the precursor fibre can be carried out from the end faces of the packing, causing the reaction to advance through inside the channels. Numerous processes can be used, in particular when the reagent is a gas and the reaction product is a porous solid not adhering to its substrate. For example, with regard to iron fibres:

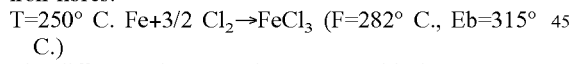
T=250° C. Fe+3/2 $Cl_2 \rightarrow FeCl_3$ (F=282° C., Eb=315° C.)

The difference between the gaseous chlorine pressure in equilibrium with the metal and the pressure of operating conditions applied at the fibre input enables the chlorine permanently to reach the interface of the fibres and to be consumed. The removal of the $FeCl_3$ can be obtained by cyclic evaporation, or under gravity with vibration. The removal of the core of the fibres may take place over several steps of attack and elimination of the formed product.

Among the hydrolysable polymers mention may be made inter alia of the polyesters derived from glycolic acid, from lactic acid, from cellulose, and in particular polyglycolic acid or its copolymers with lactic acid, with ε-caprolactone or with trimethylene carbonate. Preferably, a polymer is chosen whose hydrolysis is rapid at a temperature of 80 to 100° C.

According to an improvement of the invention, the channel precursor fibres comprise a sub-layer (sub-layer vis-à-vis the monolith, outer layer vis-à-vis the core of the fibre) of a compound such as a water-soluble polymer, a hydrolysable polymer, a water-swelling polymer, or a wax or a metal melting at a temperature higher or slightly higher than the temperature of the manufacturing process of the composite.

This sub-layer surrounds the core of the fibre.

This sub-layer is called an ablative layer in this document.

This ablative layer is made by deposit on the core of the fibre before forming the monolith preform.

This so-called ablative layer may be intermediate between the core of the fibre and the spacer.

An ablative layer of wax or metal melts into a liquid product of low viscosity.

This pre-treatment has two advantages:
  the expansion differential between the fibre and the matrix can be offset for example by evacuating the liquid molten wax.
  The disappearance, degradation or evacuation of the ablative layer provides access to the core of a packing, optionally a bulk packing, made from low cost fibres, polyolefins, cellulose acetate, etc. . . . . It is therefore possible to provide access thereto for a reagent liquid (acid hydrolysis solution, reinforcing nanosol etc. . . . ), or a drying gas.

Among the existing waxes it is possible, without this list being exhaustive, to use: paraffins, fatty acids higher than C12, the esters of fatty acids such as the esters of glycerin, carnauba wax, aliphatic or aromatic waxes derived from the hydrocarbon industry.

The ablative layer may for example represent between 1% and 40% of the cross-section of the fibre coated with this sub-layer. The core of the fibre, in this case, may advantageously ensure the mechanical strength of the filament According to another embodiment of this manufacturing pathway, it is possible to form the monolith separating the capillary channels using a process causing the formation of two families of pores, a family of mesopores and a family of interconnected macropores such as described in the publications by N, Ishizuka and Holloway R cited at the start of this description. This improvement provides major advantages:

The moist silica gel created by these processes around the channel precursor fibres is highly permeable to fluids and in the moist state allows the circulation through the packing mass of a liquid or gas preferably through its inlet and outlet sides.

This circulating fluid inter alia can have the role of modifying the porous structure of the bimodal gel and hence of the final packing.

It may have the role of bringing a reagent into contact with the fibre causing its elimination.

This elimination may be achieved using the previously described methods, in particular by hydrolysis, dissolution or gasification.

It may allow exchanging of mother liquors of the gel by an organic fluid whose drying is less destructive for the gel structure.

It may allow drying of the packing by circulating a gas or supercritical fluid before eliminating the channel precursor fibres.

The high porosity of the walls of the monolith obtained is favourable for rapid completion of diffusion processes between the channels.

The macropores may preferably represent a sufficient fraction of porous volume of the solid mass of the monolith, sufficient to ensure the percolation and interconnection thereof so as to allow the flow of a fluid. Preferably, this fraction is higher than 40% and further preferably higher than 70%.

It will be noted that at all events when the mass of the packing is formed of nanoscopic particles of agglomerated amorphous silica (silica gel) it can be reinforced before drying either by ripening at basic pH, or by depositing or precipitating amorphous silica thereupon in an aqueous phase so as achieve mechanical reinforcement by rigidifying its structure.

It is difficult to carry out precipitation of silica in a dense object, since the solubility of silica in water is very low (400 ppm at 100° C.). Permissible supersaturations of the order of 500 ppm, can only reinforce the outer layers of a bulk object since the weak diffusive flow is instantly precipitated in contact with the high specific surface area of the packing. By bulk is meant herein the porous mass of the monolith.

One answer to this problem could be formulated as follows:

This deposit or precipitation can be performed by placing the gel in close contact with nuclei or seeds of amorphous silica of very small diameter, from 2 to 4 nm for example, or nanosol, in concentrated solution under conditions of low ionic strength (molar content of salt less than 0.1 to 0.15 N).

These nuclei, on account of their very small diameter and the effect of surface tension forces, are in equilibrium with a concentration of silica in aqueous pause that is greater than that in equilibrium with the constituent silica particles of the packing of specific surface area larger than 350 m²/g for example.

The solubility S of the particles of diameter d (Ralph K. Iler, The chemistry of Silica, 1979, p 50) is written:

$$S/So = \exp(4EV/R/T/d)$$

The surface tension E for silica is of the order of 46 erg/cm² (Iler p 54).

These nuclei may be created by acidification up to pH 9 of a dilute solution of sodium silicate, either by an acid, or by an ion exchanger. These nanosols are sufficiently stable to exist for several tens of minutes in solution, at notable concentrations for example 5 to 20 g/l in silica equivalent.

Their contact and their circulation at 90-100° C. in very close proximity with the walls of the capillaries allows the particles of the nanosol to diffuse via Brownian motion inside the constituent gel of the monolith down to major depths, of several hundred microns, and to re-dissolve thereat and deposit reinforcing silica at depth on the surface of this constituent gel of the monolith.

The depth of penetration, i.e. of reinforcement of the gel depends upon the diffusivity of the nanosol (between 0.5 and 1.0 10-9 m2/s, Einstein equation)) and on the speed of kinetic phenomena of redissolution-reprecipitation of the amorphous silica between the nanosol and the gel.

It is necessary to operate with nanosols and packing materials impregnated with an aqueous solution of low ionic strength and low basic pH (9 to 10), so as to avoid coalescence of the silica particles between each other.

The driving force of the process is the much greater difference in driving concentration of diffusion allowed by the nanosol.

A silica packing can be hydrophobized or surface modified by a silane such as hexamethyl disilazane, silanes allowing coupling to $C_8$ or $C_{18}$ straight carbon chains, or any other known silane, or any other method for treating a silica surface known in the state of the art.

A packing in alumina can be co-precipitated or impregnated with additives, its acid-base status can be adjusted.

Without departing from the scope of the invention, the channel precursor fibre may be formed of a capillary tube, a fibre of various geometric cross-sections (square, hexagonal, etc).

Without departing from the scope of the invention the channel precursor fibre may itself be porous.

Another process for manufacturing the monolithic material comprises the forming and assembling of thin films. This process uses as base material thin films or sheets of material. This material may be a precursor of amorphous silica, such as a silicon resin.

The process can be implemented by printing channels via etching, photo-etching, drawing or moulding in a sheet of silicone elastomer, and stacking or rolling of the sheets into the shape of the desired final packing. Subsequent treatment by pyrolysis and oxidation transforms the silicon to amorphous silica crossed by free channels.

In this case, a multicapillary packing is prepared by the assembly of a large number of multicapillary packing elements.

FIG. 1 is a cross-sectional view of cylindrical multicapillary packing for chromatography according to the invention, following a direction perpendicular to its major axis.

It comprises a porous mass of amorphous silica 2 and void capillary channels 1 in which the fluid passing through the packing 3 is able to circulate freely.

In the described case, the capillary channels are straight, parallel and regularly spaced. The different channels have morphologies and diameters that are as identical as possible. Each channel passes through the monolithic material i.e. its ends are open on each side 4 and 5 of the cylindrical packing, allowing the circulation of the fluid from the inlet side towards the outlet side.

Said material can therefore be used in a chromatographic column.

Figure 2:
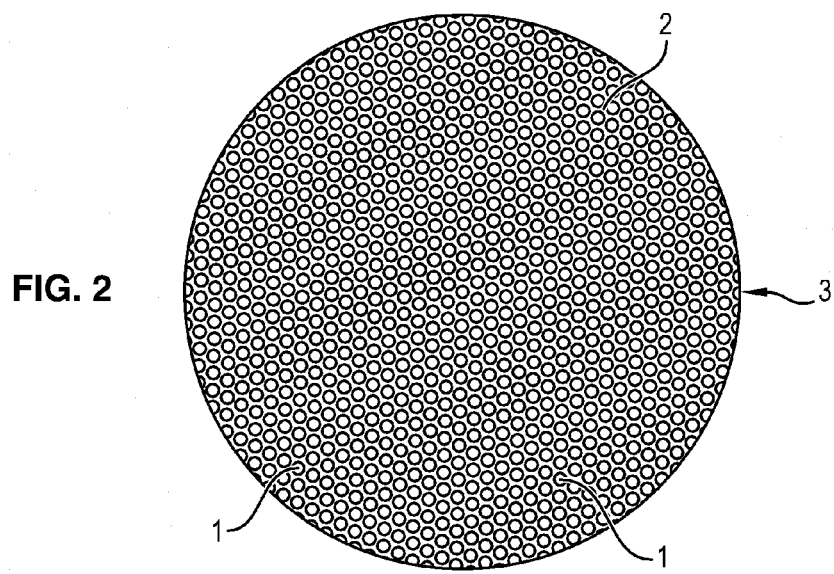
FIG. 2 is an overhead view of one side of the cylindrical packing in FIG. 1.

FIG. 2 is an overhead view of one side 5 of the cylindrical packing seen along direction 6. The openings of individual capillary channels 1 can be seen in the porous mass 2.

Figure 3:
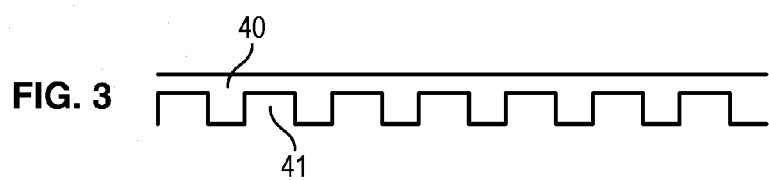
FIG. 3 is a cross-sectional view of a film of silicone elastomer wherein channels are etched which, after stacking or rolling, are intended to form the capillary channels.

FIG. 3 is a cross-sectional view of a film of a silicone elastomer 40 in which transverse channels 41 are arranged that are parallel and perpendicular to the plane of the figure, whose stacking or rolling into cylinder shape about an axis parallel to the channels forms a preform of the final packing.

The preform is then heated and oxidized to obtain the multicapillary packing of amorphous silica with high specific surface area.

Figure 4:
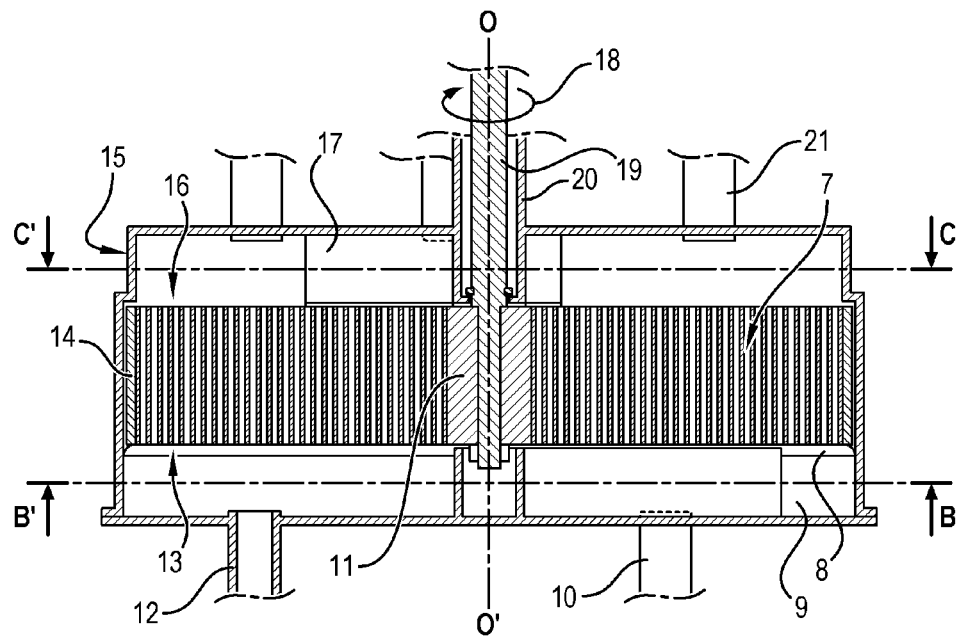
FIGS. 4, 5 and 6 are block diagrams of a continuous annular chromatograph using multicapillary packing according to the invention.
Figure 5:
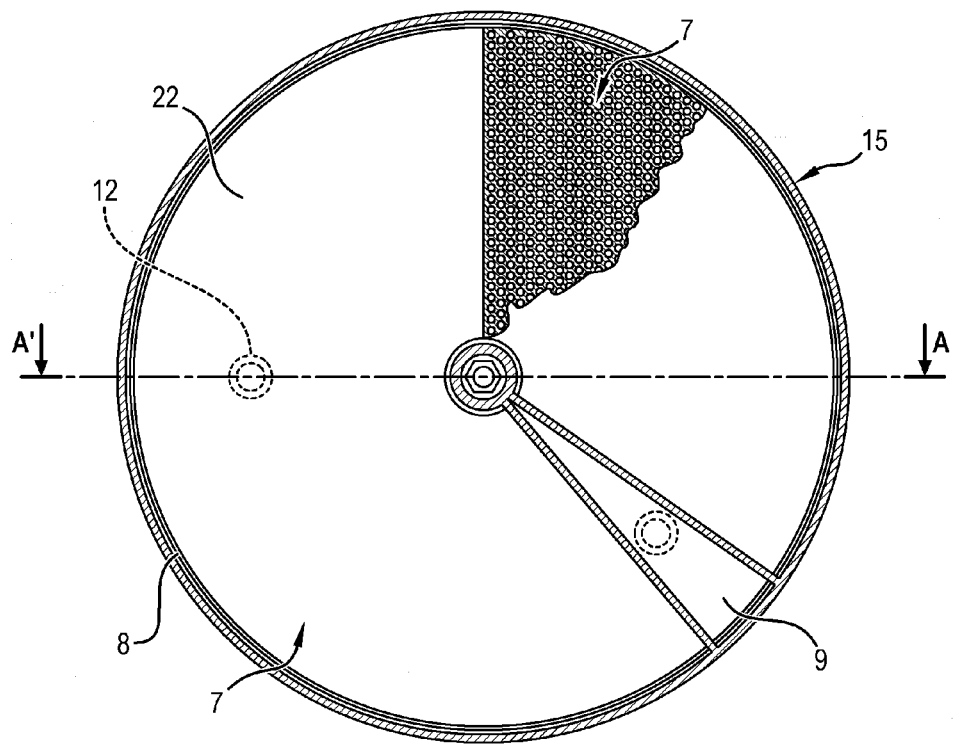
Figure 6:
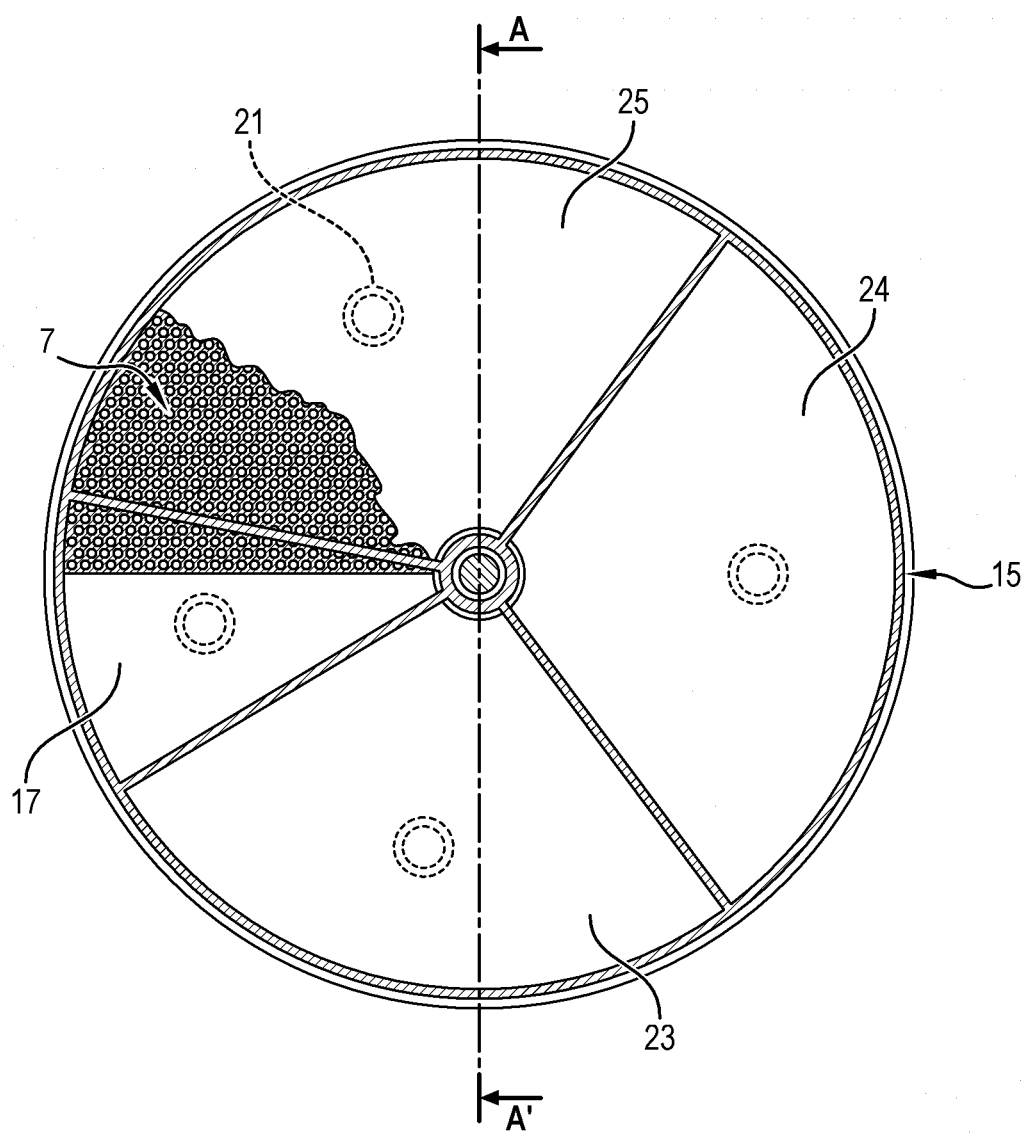

FIGS. 4, 5 and 6 are block diagrams of a continuous annular chromatograph using a multicapillary packing for the separation of two products. Diagram 4 is a cross-section of the instrument along AA'. Diagram 5 is a cross-section of the instrument along BB' (i.e. the upstream part of the chromatograph), diagram 6 is a cross-section of the instrument along CC' (i.e. its downstream part).

Said annular chromatograph comprises a cylinder of multicapillary packing 7 whose capillary channels are parallel to its major axis. Its two sides 13 and 16 act as support for the fluid inlet and outlet assemblies. A representative part of the packing 7 can be seen in cross-section in FIG. 5.

This instrument further comprises fluid inlet 9, 22, and outlet assemblies 17, 25, 24 and 23 which are in the form of angular sectors separated by vertical walls which slide over the packing by means of flexible seals without damaging the packing, or are positioned very close thereto i.e. a few microns or tens of microns away without any direct contact and therefore without any wear part, imparting the seal or the plate separating two sectors with sufficient thickness so that the leak flow rate caused by play is smaller than the flow evacuated towards the downstream side by the fraction of packing lying under the seal.

Owing to the low pressure drop of the multicapillary packing, the relative pressure differences between the different feed sectors of the chromatograph may be relatively high and hence easily adjusted It is effectively easier to adjust a pressure difference of 0.03 bar between two chambers brought to 0.3 bars relative (relative to the atmosphere) than the same pressure difference between two chambers brought to 3 bars (relative). The leak flow rate of the feed and eluting fluids between the different sectors is directly proportional to the square root of the difference in pressure between these sectors, and not to the absolute pressure prevailing therein.

For precise adjustment of this distance, the packing is sealed to an external cylinder which may be in a machined material for example.

The inlet and outlet assemblies are fixed relative to one another.

Each sector on the inlet and outlet sides is connected to an inlet port 10, 12 and outlet port 21.

The cylindrical packing and its inlet and outlet assemblies move relative to one another in a circular movement 18 about the axis OO'. This movement is imposed upon the packing by a drive shaft 19 via a central shaft 11 to which the packing is attached.

The packing rotates inside a ferrule 15, 20 closely adjusted to its outer diameter. The feeding of the mixture to be separated via port 10 and of the eluting fluid via port 12 takes place through different sectors 9 and 22 of its upstream surface, and the collection of the different eluted fractions similarly takes place on different sectors of its downstream surface (sectors 17 and 24 for the two separated components and 23 and 21 for the eluent).

The constancy of residence time for each component in the packing allows the collection thereof at determined angular distances of the feed sector. The continuous flow in the feed sectors in this case produces a continuous production flow in the outlet sectors.

Figure 7:
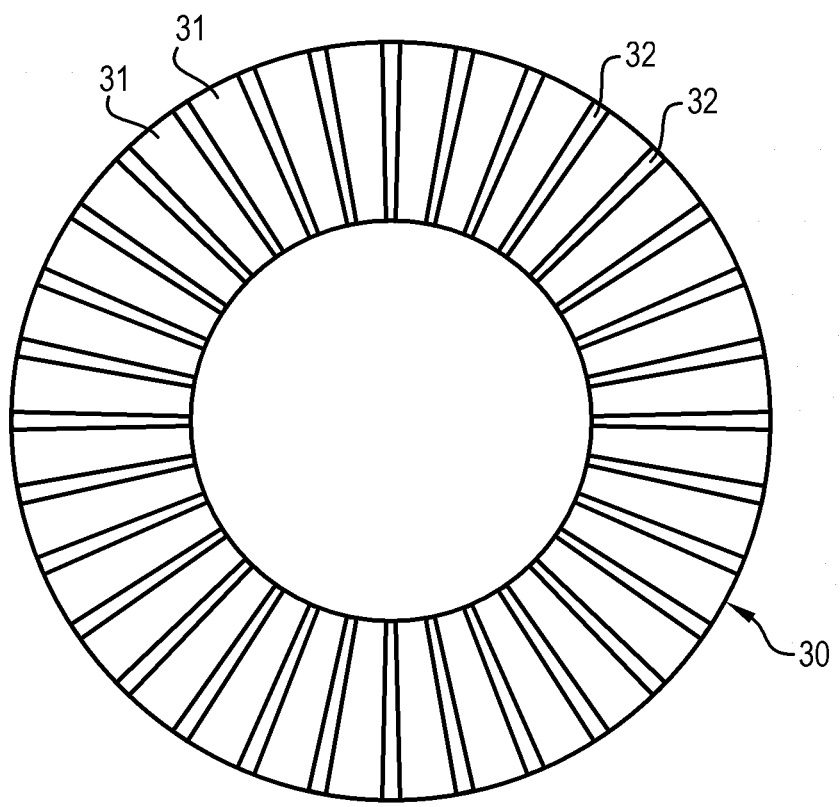
FIGS. 7 and 8 are block diagrams of a radial multicapillary packing for radial annular chromatograph.

FIG. 7 is a schematic cross-sectional view of a radial multicapillary packing 30 in which the channels 31 extend radially from inside the packing towards its periphery, separated by walls 32.

Figure 8:
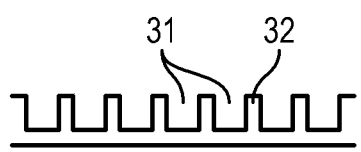

FIG. 8 is a radial view of a constituent element of the same packing. In this case, the packing is formed of a coaxial stack of discs 30 so as to create the conduits for forming capillary channels.

The continuous annular chromatographs just described lend themselves particularly well to gas chromatography, the vector gas able to be cooled and recycled or continuously re-circulated by means of low-cost apparatus such as fans, without requiring compressors to be included in the circuit.

In addition, the continuity of the flows avoids the need for gas valves with sequential opening as required by discontinuous industrial installations.

Finally, the low absolute pressures conveyed allow sealed functioning and easy adjustment of the assembly.

EXAMPLES

Different modes are described below for preparing capillary channels in the monolithic porous material of the invention.

Example 1: Preparation of a Multicapillary Packing in Silica Using a Sol Gel Process In this embodiment the fibres are formed of a hydrolysable polymer and are assembled into a bundle. The bundle is immersed in a silica gel precursor solution, a solution which is caused to gel around the fibres; the fibres are then eliminated by hydrolysis to soluble species of low molecular weight.

A Caprosyn Tyco Healthcare monofilament, grade 5 (outer diameter of about 150 µm) is immersed in an aqueous solution containing 10% of a polyvinyl alcohol and 15% by weight of glass micro-beads of diameter between 0 and 40 µm supplied by Potters Ballotini. The monofilament is then dried. In this manner the outside of the Caprosyn filament is coated with glass micro-beads which act as spacers adhering to its surface through the action of the PVA which acts as adhesive.

A bundle is fabricated by assembling 9 of these fibres laterally together in a rectangular section with sides of 2000 µm by 250 µm and length of 20 mm. The bundle is formed in a rectangular channel of the above-mentioned dimensions, the depth being 250 µm, hollowed out of a Teflon sheet 20 mm×20 mm×10 mm.

The bundle of Caprosyn fibres is impregnated with a mixture of Ludox TM50 (Grace trademark, sol of amorphous silica particles 22 nm in diameter, having a specific surface area of 140 m2/g, containing 50% by weight of silica) and 98% sulfuric acid in adequate proportions to obtain a 10% by weight solution of sulfuric acid relative to the water. The liquid must fill the entirety of the packing, which must be immersed therein. The packing is closed with an upper planar sheet, or cover, of Teflon of identical dimensions to the previous sheet, screwed thereupon.

The assembly is brought to 100° in a hot water bath.

The sol gels very rapidly under these conditions, in 10 mn to one hour. It produces a non-reinforced packing moulded around the fibres.

Each end of the bundle projecting beyond the Teflon sheets is cut with a very fine blade to release the channel section.

The device is left to react 48 hours at the temperature of 100° C. to dissolve the fibres by hydrolysis.

The packing is then opened by removing the cover.

A second cover in Teflon of identical outer dimensions to the previous cover comprising and allowing a free channel 3 mm thick and 5 mm wide to be provided above the packing is positioned and centred above the length of the channels and joined to the base carrying the same. This cover allows the circulation of a gas flow and contact thereof with the entire length of the channels.

The assembly is brought to 112° C. and a flow of steam at 0.5 ml/s is maintained through the free channel purging for 24 hours.

The temperature is then brought to 180° C. for 12 hours under the same steam purging.

The temperature is finally brought to 250° C. for 12 hours, under the same steam purging, then the packing is cooled to ambient temperature.

The upper cover is then detached and the packing released.

Figure 9:
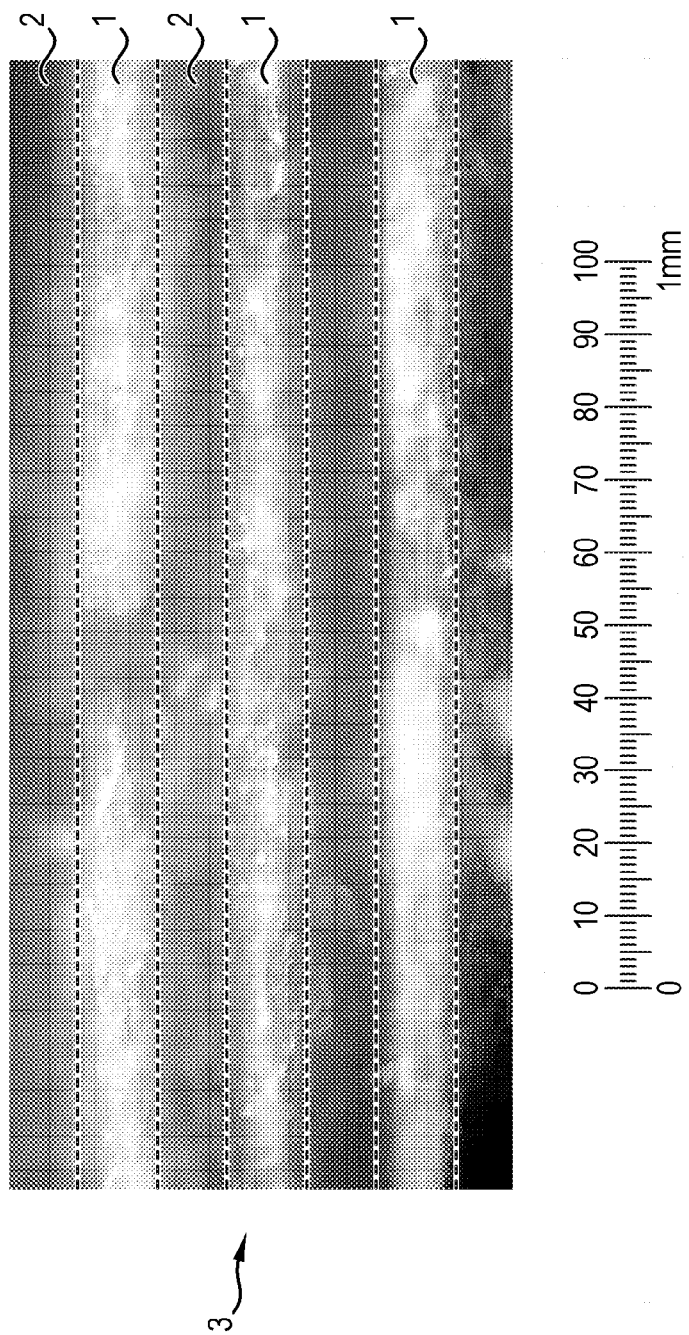
FIG. 9 is a photograph of a cut made through a monolithic porous material prepared according to the invention.

FIG. 9 is a photograph of a cut made in a packing 3 obtained using the method just described.

As can be seen, the channels 1 surrounded by porous silica 2 are regular and uniform.

Example 2: Preparation of a Multicapillary Packing in Silica Using a Sol Gel Process In this embodiment, the fibres are formed of a hydrolysable polymer, assembled into a bundle. The bundle is immersed in a silica gel precursor solution, the solution then being caused to gel around the fibres and the fibres are eliminated by hydrolysis to soluble species of low molecular weight. This fabrication method also comprises reinforcement of the silica gel by depositing silica on the surface of its constituent particles before drying.

A Caprosyn Tyco Healthcare monofilament, grade 5 (outer diameter of about 150 μm) is immersed in an aqueous solution containing 10% of a polyvinyl alcohol and 15% by weight of glass micro-beads of diameter between 0 and 40 μm supplied by Potters Ballotini. The monofilament is then dried. In this manner, the outside of the Caprosyn filament is coated with glass micro-beads which act as spacers adhering to its surface via the action of the PVA which acts as adhesive.

A bundle is made by assembling 7 of these fibres in a rectangular section of sides 1700 μm by 250 μm and length of 100 mm. The bundle formed in a square channel of the above-mentioned dimensions, the depth being 250 μm, hollowed out of a sheet of 316L stainless steel 100 mm×20 mm×10 mm, or module.

On a planar face of the Teflon cover of the module, a solution of polyglycolic acid or polyglycolide in hexafluoroisopropanol (HFIP) is deposited so as to leave on this face after drying a thickness of polyglycolide of about 5 micrometers.

The bundle of Caprosyn fibres is impregnated with a mixture of Ludox TM50 (Grace trademark, sol of amorphous silica particles 22 nm in diameter, and specific surface area of 140 m2/g, containing 50% by weight of silica) and 98% sulfuric acid in adequate proportions to obtain a 10% by weight solution of sulfuric acid relative to the water. The liquid must fill the entirety of the packing which must be immersed therein. The packing is closed by an upper planar sheet of Teflon, or cover, of identical dimensions to the previous sheet, screwed thereupon the side coated with polyglycolide against the packing.

The assembly is brought to 100° C. in a hot water bath.

The sol gels very rapidly under these conditions, in 10 mn to one hour. It produces a non-reinforced packing moulded around the fibres.

The device is left to react for 24 hours.

Each end of the bundle projecting beyond the Teflon sheets is cut with a very fine blade to release the section of the channels.

After this operation, the cover is removed releasing the upper surface of the gel.

This operation and the washings are performed by maintaining the non-reinforced packing immersed in its liquid treatment bath between each step, and limiting nearby turbulence inasmuch as possible.

The device is left to react 7 hours at the temperature of 100° C. immersed in a bath of 16% sulfuric acid in water so as to complete the dissolution of the fibres by hydrolysis.

The packing is washed with two consecutive five-hour stripping operations with one liter of demineralised water at 100° C. previously saturated with amorphous silica, then with a buffer solution diluted to pH 9 at 100° C. for five hours, then with three consecutive five-hour stripping operations with one liter of demineralised water at 100° C. previously saturated with amorphous silica.

A second cover in Teflon of outer dimensions identical to the packing support, comprising and allowing a free channel 0.25 mm thick and 1.7 mm wide to be provided above the packing is positioned and centred over the length of the channels and joined to the base carrying the same. This cover allows the circulation of a flow of liquid and contacting thereof with the entire length of the channels.

This upper channel is fed via one of its ends with an aqueous suspension containing 1.4% silica sol with very high specific surface area (1000 to 1700 m2/g) stabilized at pH9. This solution or aqueous suspension is obtained by mixing a 0.4 M solution of boric acid with sodium silicate in concentrated solution of density 1.34 so as to obtain a 0.15 M solution of sodium ions that is used immediately. The feed is maintained at a temperature of 100° C. so that the entire wet part of the immersion process of the fibre until reinforcement of the gel is conducted at a constant temperature of 100° C. In this manner it is possible to ensure perfect morphology of the packing. The reinforcing mechanism is Oswald ripening, the smallest particles dissolving whilst the largest grow in diameter owing to the greater solubility of the silica in equilibrium with particles of narrow diameter. The flow is maintained at a velocity of 3 cubic millimeters/s. The reinforcement lasts 60 mn.

The packing is then washed with a dilute aqueous solution of sulfuric acid at pH2, then with demineralised water. The cover is removed and the packing is rapidly dried under a direct steam of dry air at 105° C., then brought to 400° C. in air for one hour.

A cover is replaced on the packing. This cover has the same dimensions as the previous cover but is made in 316L stainless steel.

The packing can be hot-rehydrated in an acid or basic aqueous solution using any known technique.

The packing can be used as such for chromatography.

It can be hydrophobized or surface modified with a silane such as hexamethyl disilazane or any other known silane, or any other method.

Example 3: Preparation of a Multicapillary Packing in Silica Using a Sol Gel Process In this embodiment, the fibres are formed of a hydrolysable polymer, assembled in a bundle. The bundle is immersed in a silica gel precursor solution, a solution which is caused to gel around the fibres, and then the fibres are eliminated by hydrolysis to soluble species of low molecular weight. This manufacturing process may also comprise reinforcing of the silica gel by depositing silica on the surface of its constituent particles before drying.

A Caprosyn Tyco Healthcare monofilament, grade 5 (outer diameter of about 150 μm) is immersed in an aqueous solution containing 10% of a polyvinyl alcohol and 15% by weight of glass micro-beads of diameter between 0 and 40 μm supplied by Potters Ballotini. The monofilament is then dried. In this manner, the outside of the Caprosyn filament is coated with glass micro-beads which act as spacers adhering to its surface via the action of the PVA which acts as adhesive.

A bundle is manufactured by assembling 49 of these fibres in a square section with sides of 1700 μm and length of 100 mm. The bundle is assembled within a square channel of the above-mentioned dimensions (square section) hollowed out of a 316L stainless steel sheet 100 mm×20 mm×10 mm.

On one side of the Teflon cover of the module, a solution of polyglycolic acid or polyglycolide in hexafluoroisopropanol (HFIP) is deposited so as to leave on this side after drying a thickness of polyglycolide of about 5 micrometers.

The bundle of Caprosyn fibres is impregnated with a mixture of Ludox TM50 (Grace trademark, sol of amorphous silica particles 22 nm in diameter, specific surface area of 140 m2/g, containing 50% by weight of silica) and 98% sulfuric acid in adequate proportions to obtain a 10% by weight solution of sulfuric acid relative to the water. The liquid must fill the entirety of the packing which must be immersed therein. The packing is closed with an upper planer sheet, or cover, of Teflon of identical dimension to the previous sheet, screwed thereupon the side coated with the polyglycolide against the packing.

The assembly is brought to 100° C. in a hot water bath.

The sol gels very rapidly under these conditions, in 10 mn to one hour. It produces a non-reinforced packing moulded around the fibres. The device is left to react for 12 hours.

Each end of the bundle projecting beyond the Teflon sheet is cut with a very fine blade to release the section of the channels.

After this operation, the cover is removed releasing the upper surface of the gel.

This operation and the washings are performed maintaining the non-reinforced packing immersed in its liquid treatment bath between each step, limiting nearby turbulence inasmuch as possible.

The device is left to react 24 hours at the temperature of 100° C. immersed in a bath of 16% sulphuric acid in water to dissolve the fibres by hydrolysis.

This treatment is completed by immersion in 40% nitric acid at 100° C. for five hours.

The packing is washed with two consecutive five-hour stripping operations in one liter of demineralised water at 100° C. previously saturated with amorphous silica, then with a dilute buffer solution diluted to pH9 at 100° C. for five hours, then with three consecutive five-hour stripping operations with one liter of demineralised water at 100° C. previously saturated with a amorphous silica.

A planar cover is replaced over the packing. This cover has the same dimensions as the first but is made in 316L stainless steel.

The silica of the packing at this stage ill resists drying on account of the weak bonds between the individual gel particles. To increase the force of this bonding, silica is deposited around the particles and particularly around their point of contact in sufficient quantity.

For this use, the packing is fed via one of its ends with a 1.4% aqueous solution of silica sol with very high specific surface area (1000 to 1700 m2/g) stabilized at pH9. This solution or aqueous suspension can be obtained by mixing a 0.4 M boric acid solution with sodium silicate in concentrated solution of density 1.34 to obtain a 0.15 M solution of sodium ions that is used immediately. The feed is maintained at a temperature of 100° C. The flow is maintained at a velocity of 7 cubic millimeters/s for the packing. The reinforcement lasts 60 mn.

The packing is then washed with a dilute aqueous solution of sulfuric acid at pH 2, followed by washing with distilled water, to eliminate all the impurities and basicity of the packing. It is then dried in a stream of dry hot air at a temperature of 120° C.

The packing can be used as such for material exchange. It can be activated by pyrolysis.

It can be hydrophobized or surface modified with a silane such as hexamethyl disilazane or any other known silane, or any other method.

Example 4: Preparation of a Multicapillary Packing in Polymer and Porous Carbon The present example is given by way of indication to evidence the great ease of use and flexibility of application of the process according to the invention to prepare monoliths having rectilinear capillary channels parallel to one another and intended for chromatography.

The starting material is a wire in a tin and lead alloy in proportions of 60%, 40% respectively. Its diameter is 7/10 mm. The wire is cut into rectilinear needles 15 cm in diameter coated with a thin layer by immersing in a mixture of a non-polymerized epoxy resin and powder silica in suspension in tetrahydrofuran (20% araldite, 80% THF, and a volume of Aerosil 380 equivalent to ¾ of the volume of the solution). The needles are placed 24 hours close to a heat source (50° C.). They are then cut into lengths of 100 mm and assembled in a bundle of diameter about 14 mm in a glass tube of length 80 mm and inner diameter of 18 mm that is previously prepared.

The inner wall of this tube is previously coated, before insertion the bundle, with a layer of polyester of thickness about 2 mm, polymerized in situ.

A liquid polyester resin and its polymerization activator are then poured into the tube via the interstices of the needles so as to fill this void space completely. The resin is polymerized for 24 hours at ambient temperature.

The composite thus formed is released by sectioning the needles over a length of 10 mm either side of the glass tube, flush with its ends and perpendicular to the needles.

The bundle is immersed in an oil bath at 190° C. until melting of the needles and the molten metal is easily eliminated via light circulation of pressurized air.

Example 5

In this variant, polymeric fibres precursors of the channels are assembled in a bundle, the bundle is immersed in a silica gel precursor solution, this solution being caused to gel around the fibres, then the fibres are eliminated by pyrolysis and combustion. The silica gel can be reinforced by depositing silica on the surface of its constituent particles before dying.

A Nylon monofilament (outer diameter of about 150 µm) is immersed in an aqueous solution containing 10% of a polyvinyl alcohol and 15% by weight of glass micro-beads of diameter between 0 and 40 µm supplied by Potters Ballotini. The monofilament is then dried. In this manner, the outside of the filament is coated with glass micro-beads which act as spacers adhering to its surface via the action of the PVA which acts as adhesive.

A bundle is fabricated by assembling these filaments into a bundle of rectangular section, 1700 µm in width, 250 µm in depth and 100 mm in length. This bundle is created by rolling inside a said channel precisely machined in a sheet of 316L stainless steel 100 mm×20 mm×10 mm. This bundle of polyester fibres is impregnated with a mixture of 24.3 g of tetramethylsiloxane, and 57.6 ml of a 1% ammonia solution in water. The liquid must fully wet and fill the packing.

The packing is closed with an upper cover formed of a planar sheet of stainless steel of identical dimensions to those of the base stainless steel sheet, screwed thereupon, on which a thickness of about 5 micrometers of paraffin melting at 62° C. has previously been deposited.

The mixture is left to polymerize and gel for 24 hours at 42° C.

The two ends of the packing are cut flush with the steel sheet to release the section of packing.

The packing has a length of 100 mm.

The packing and its jacket are brought to 90° C.

The cover is removed and the packing is dried in dry air at a temperature of 105° C. for 2 hours.

The resulting product is heated to 650° C. in an atmosphere of air at a rate of 100° C. per hour starting from ambient temperature, for conversion thereof to a multicapillary packing by burning the polymeric fibres.

Once cooled, the packing is again closed on its upper part by a planar sheet of stainless steel, or cover, of same dimensions screwed onto the one containing the packing.

Example 6

A wire of a mixture of Pb, Sn, Bi in weight proportions of 32, 15, 53 melting at 96° C., is produced with a diameter of 0.5 mm.

This wire is cut into rectilinear needles of length 120 mm.

200 g of Silica Gel for chromatography (Acros reference 24167) is ground down to a mean particle size of about 10 µm.

The powder is gradually placed in suspension 500 ml of a mixture of 200 ml of silica sol TM50 by Grace containing 50% dry matter, and 300 ml of demineralised water maintaining the pH at 9.5 with a continuous supply of sodium hydroxide N.

1.0% of a 10% solution of perfluoroctane sulfonate is added.

Once the placing in suspension is completed, the metal wire is immersed in the suspension of silica held under agitation. It is suspended in a flow of moist air at 80° C. saturated by passing in a 10% solution of acetic acid in water for 1 h so that the sol gels without evaporating. It is then instantly dried under a stream of dry air at 80° C.

The needles are then cut to an exact length of e 100 mm clearing each side, and they are arranged in a hexagonal housing of sides 2.6 mm and length of 100 mm formed of two semi-shells hollowed out of a 316L stainless steel sheet 20×10×100 mm. The needles are arranged parallel to each other and regularly in seven successive layers on the lower semi-shell.

The two semi-shells are screwed onto each other.

A mixture is prepared of Ludox TM50 (Grace trademark, sol of amorphous silica particles, 22 nm in diameter, specific surface area of 140 m²/g, containing 50 weight % silica) and of 98% sulphuric acid in adequate proportions to obtain a 5% sulfuric acid solution relative to the contained water.

The bundle of metallic needles is impregnated with this mixture. The liquid must fill the entirety of the packing which must be immersed therein.

The mixture is held at 90° C. until complete gelling of the sol.

The steel shell containing the bundle is extracted from the gel, its ends are released and it is arranged vertically in a boiling hot water bath at 100° C. The metal melts and flows naturally out of the bottom of the bath releasing the capillary channels.

The monolith is washed with deionized water percolated through the free channels.

The monolith thus obtained can be used directly for aqueous phase liquid chromatography.

It can be activated by pyrolysis.

It can be hydrophobized or surface modified with a silane such as hexamethyl disilazane or any other known silane, or any other method.

Example 7

A wire of a mixture of Pb, Sn, Bi in weight proportions of 32, 15, 53 melting at 96° C., is produced with a diameter of 0.5 mm.

This wire is cut into rectilinear needles of length 120 mm.

These needles are immersed in a solution in water of 0.5% polyvinyl alcohol containing 0.05% of surfactant FC-4430 by 3M, and dried at a temperature of 80° C.

200 g of activated alumina neutral for chromatography (Acros reference 19041) is ground down to a mean particle size of about 10 µm.

An alumina sol is prepared in the following manner.

About 700 g of non-hydrated aluminium nitrate (Al(NO3)3, 9 H2O) for analysis—Acros) are dissolved in one liter of deionized water at 22° C. under agitation until saturation. 1520 g of urea are added to the mixture and solubilized.

The solution is held at 22° C. for one hour and passed through a 0.22 µM Millipore filter.

The solution obtained is held at 90° C. for 12 hours.

The alumina powder is gradually placed in suspension in 500 ml of this alumina sol maintaining the pH of the solution constant by adding 0.1N ammonia solution.

Once the placing in suspension is completed, the metal wire is immersed in the suspension of alumina held under agitation. It is then instantly placed and suspended in a confined atmosphere, to avoid any early dehydration, at 90° C. until the sol gels. It is then dried in a stream of dry air at 80° C.

The needles are then cut into exact lengths of 100 mm clearing either side and are arranged in a hexagonal housing of sides 2.6 mm and length of 100 mm formed of two semi-shells hollowed out of a 316L stainless steel sheet 20×10×100 mm.

The needles are arranged parallel to each other and regularly in seven successive layers.

The two semi-shells are screwed onto each other.

A second alumina sol is prepared in the same manner as previously mentioned in this example.

The bundle of metallic needles is impregnated with this sol inserted via the interstices of its free ends. The liquid must fill the entirety of the pacing which must be immersed therein.

The mixture is held at 90° C. until complete gelling of the sol.

The steel shell containing the bundle is extracted from the gel, its ends are freed and it is arranged vertically in a boiling hot water bath at 100° C. The metal melts and flows naturally to the bottom of the bath releasing the capillary channels in an alumina packing of high specific surface area.

The monolith is washed with deionized water percolated through the free channels The monolith can later be dried and activated at a temperature of 250 to 650° C.

It will be noted that in all the examples provided above, the percentages are weight percentages.

The invention claimed is:

1. A process for preparing a monolithic porous material based on amorphous silica or activated alumina comprising rectilinear capillary channels parallel to one another, comprising the steps of:
   providing a bundle of channel precursor fibres whose diameter is equal to the diameter of the capillary channels,
   forming a porous matrix of amorphous silica or activated alumina around the fibres,
   eliminating the fibres so as to form the capillary channels extending through the porous matrix.

2. The process of claim 1, wherein the channel precursor fibres comprise an ablative layer of a coating material that is removed during a first fibre elimination treatment step.

3. The process of claim 1, wherein the channel precursor fibres are coated with a spacer before forming the bundle to ensure a minimum thickness of the porous matrix between two adjacent channels.

4. The process of claim 1, wherein the porous matrix of amorphous silica has a proportion of macropores greater than 40% of the total porous volume of the monolithic material, wherein the macropores allow the circulation of a fluid in the monolithic porous material.

5. The process of claim 1, wherein the fibres are formed of a hydrolysable polymer, the fibres are assembled in a bundle, the bundle is immersed in a silica gel precursor solution, the solution being caused to gel around the fibres, and the fibres are eliminated by hydrolysis to soluble species of low molecular weight.

6. The process of claim 1, wherein the channel precursor fibres are metal wires with low melting point coated with a film of silica or activated alumina, assembled in a bundle, the bundle is immersed in a silica gel or activated alumina precursor solution, the solution being caused to gel around the fibres, and the fibres are eliminated by melting and draining the molten liquid outside the monolithic porous material.

7. The process of claim 1, wherein the porous matrix is amorphous silica, and the amorphous silica is reinforced by depositing silica on the surface of its constituent particles, before drying thereof.

8. The process of claim 1, wherein the porous matrix comprises silica gel.

9. A process for preparing a monolithic porous material based on silica gel comprising rectilinear capillary channels parallel to one another, comprising the steps of:
   providing a bundle of channel precursor fibres whose diameter is equal to the diameter of the capillary channels,
   forming a porous matrix of silica gel around the fibres, and
   eliminating the fibres so as to form the capillary channels through the silica gel matrix.

* * * * *